United States Patent [19]

Brooks et al.

[11] Patent Number: 4,702,252
[45] Date of Patent: Oct. 27, 1987

[54] CATHETERS

[75] Inventors: Kenneth J. Brooks, Lancing; Michael A. Wilkinson, East Preston; Peter H. Hannam; Neil A. Whiteside, both of Worthing, all of England

[73] Assignee: Smiths Industries Public Limited Company, London, England

[21] Appl. No.: 822,839

[22] Filed: Jan. 27, 1986

Related U.S. Application Data

[63] Continuation-in-part of Ser. No. 541,665, Oct. 13, 1983, abandoned.

[51] Int. Cl.⁴ .................... A61M 29/02; A61M 25/00
[52] U.S. Cl. ..................................... 128/344; 604/103
[58] Field of Search ................. 128/344; 609/96, 97, 609/98, 99, 100, 101, 103, 104, 288

[56] References Cited

U.S. PATENT DOCUMENTS 3,416,531 12/1968 Edwards .......................... 604/282 X
3,924,632 12/1975 Cook ................................... 604/280
4,222,384 9/1980 Birtwell ............................... 604/103
4,315,512 2/1982 Fogarty ............................... 128/344

FOREIGN PATENT DOCUMENTS 693224 6/1953 United Kingdom ................. 604/96
1566674 5/1980 United Kingdom .

Primary Examiner—Pellegrino, Stephen C.
Attorney, Agent, or Firm—McAulay, Fields, Fisher, Goldstein & Nissen

[57] ABSTRACT

A dilatation catheter has a shaft comprising a tube of braided material encapsulated over a major portion of its length in an outer coating of semi-rigid inelastic material. An outer coating of elastic material extends over a minor portion of the length of the shaft at or near its distal end. An inner coating of elastic material is provided over the entire length of the inside of the tube. The distal end portion of the catheter is thereby inflatable by pressure applied from within the shaft to form a balloon. Radio-opaque markers may be provided at each end of the inflatable portion.

48 Claims, 7 Drawing Figures

CATHETERS

CROSS-REFERENCE TO RELATED APPLICATIONS

This application is a continuation-in-part of our co-pending U.S. patent application Ser. No. 541,665 filed Oct. 13th, 1983 now abandoned.

BACKGROUND OF INVENTION

This invention relates to dilatation catheters. Such catheters are well known. They are commonly used for example, in angioplasty procedures to dilate blood vessels. They comprise a catheter shaft with an inflatable balloon located near the leading end of the catheter when it is inserted into the body of the patient. This end is commonly known as the distal end. This balloon is inflated in order to effect the desired dilatation of the blood vessel. When this procedure is completed, the balloon is deflated and the catheter is removed from the body.

Hitherto, the balloon of such a catheter has consisted of an inflatable sleeve or bulb fitted on the outside of the shaft at or near the distal end. The balloon is inflated by the application of fluid passing from within the shaft. It is obviously desirable that the balloon does not inflate to an extent which would damage the blood vessel of the patient and it is an object of the present invention to provide a dilatation catheter with an inflatable portion or balloon which cannot expand beyond acceptable limits and which, when the inflatable portion is deflated, has a smooth surface flush with the shaft.

BRIEF SUMMARY OF THE INVENTION

According to one aspect of the present invention there is provided a dilatation catheter wherein a shaft of the catheter comprises a tube of material having an inelastic coating of semi-rigid material extending from the proximal end of the catheter over a major portion of the length of the shaft and also having an elastic outer coating extending over a minor portion of the length of the shaft, preferably at or near the distal end of the catheter, whereby the said minor portion is inflatable in response to the application of inflating fluid thereto, said tube comprising braided material having a preselected maximum radial extension to limit the extent of inflation of said elastic coating. Instead of, or in addition to, a coating which is inelastic over a major portion and elastic over a minor portion, the braided material may have more picks per inch in a major portion and fewer picks per inch in a minor portion. Gas flow through the braided material is prevented by having the major and minor portions contiguous with one another, the coating being bonded to the braided material, and/or by providing an inner tube or layer which is impervious. The outer surface of the catheter is preferably smooth over its entire length and the inflatable portion can be inflated to a predetermined diameter.

If the braided tube has sufficient picks per unit length in the above mentioned major portion it is unnecessary for the outer coating to vary as between the minor portion and major portion.

In this context, "sufficient" means sufficient to prevent the expansion of the braided tube over a tolerable amount when a pressure is applied to the interior of the tube such as to inflate the minor portion. A typical pressure is 150 p.s.i. (11 kg/cm$^2$). For example, the pick rate in the major portion may be in excess of 45 picks per inch (18 picks/cm) for a tube having an external diameter of 2.5 mm.

For convenience of description, the inflatable portion of the catheter is, where its context so permits, hereinafter referred to as a "balloon".

The catheter of the present invention preferably includes an inner tube defining a central lumen opening at both ends of the catheter. This allows the catheter to be passed over a guide wire during insertion and provides a means of pressure monitoring and fluid injection. The annular space between the inner tube and outer shaft of the catheter forms a passage through which an inflation fluid can pass in order to inflate the balloon. The inner tube is axially displaceable with respect to the outer shaft to accommodate its movement during inflation.

DESCRIPTION OF PREFERRED EMBODIMENTS

Figure 1:
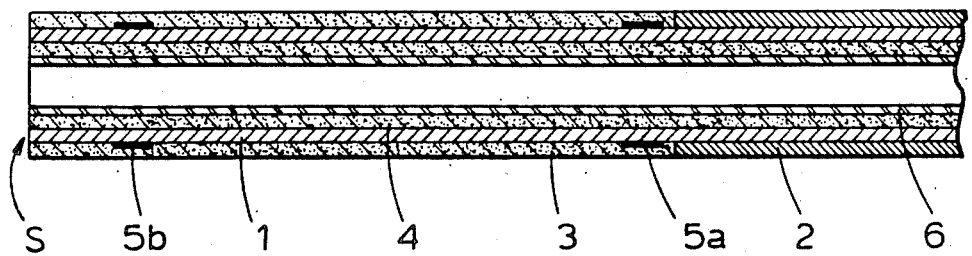
FIG. 1 is a schematic sectional view of a distal end portion of a first embodiment of a dilatation catheter according to the invention, showing a balloon portion in a deflated condition.

In the embodiment of the invention illustrated in FIG. 1, a dilatation catheter comprises a shaft generally designated S and composed of a tube 1 of braided material which may conveniently be a polyester fibre. The outer surface of the braided tube 1 is encapsulated within a coating 2 of physiologically acceptable material, preferably a plastics material such as polyester or polyether polyurethane, a silicone rubber, a plasticised polyvinylchloride (PVC) or some other suitable thermoplastic elastomer. The plastics coating 2 is interrupted near the distal end of the catheter and this interrupted minor portion is itself encapsulated within a coating 3 of an elastic material which may be an elastic polyurethane or another elastomeric material, such as silicone rubber. The elastic coating 3 is flush with the inelastic coating 2 so that the cross-sectional area of both the major portion and the minor portion are the same with the result that the profile or other surface of the shaft is smooth, that is to say the external diameter of the shaft is constant over its entire length, except that a tip may be provided as in FIG. 2 at the distal end. The portion of the braided tube encapsulated by the elastic coating 3 preferably has fewer picks per unit length than the number of picks per unit length present in the major portion of the tube 1. This makes this portion of the catheter more readily inflatable than would otherwise be the case. The portion of braided tube immediately distal to the balloon may have more picks per inch similar to the major portion of the braided tube to limit inflation or alternatively a rigid sleeve could be positioned at this point for the same purpose. An inner coating 4 of the same or similar elastic material as the outer coating 3 is preferably bonded to the inside of the braided tube over the entire length of the catheter. A radio-opaque marker portion 5a is incorporated in the shaft at or near the junction between the two outer coatings 2 and 3. Another such marker 5b is provided near the distal end of the shaft. A lining 6 may be provided. This lining may extend the entire length of the shaft as illustrated or the portion of the shaft having the balloon coating 3 need not be lined. The material of the lining may be a fluorocarbon such as polytetrafluoroethylene (PTFE) or fluorinated ethylene propylene copolymer (FEP).

If the shaft is not provided with an inner coating 4 which is elastic and impervious to the inflation fluid, or a similarly elastic impervious lining 6, or some other impervious elastic inner tube, it is essential for the outer coating 2 to be bonded to the braided tube and the major and minor portions of the braided tube must be contiguous with one another, features which are otherwise optional. This is to ensure that the braided tube has the required effect in permitting dilatation of the balloon but not the remainder of the shaft.

Figure 2:
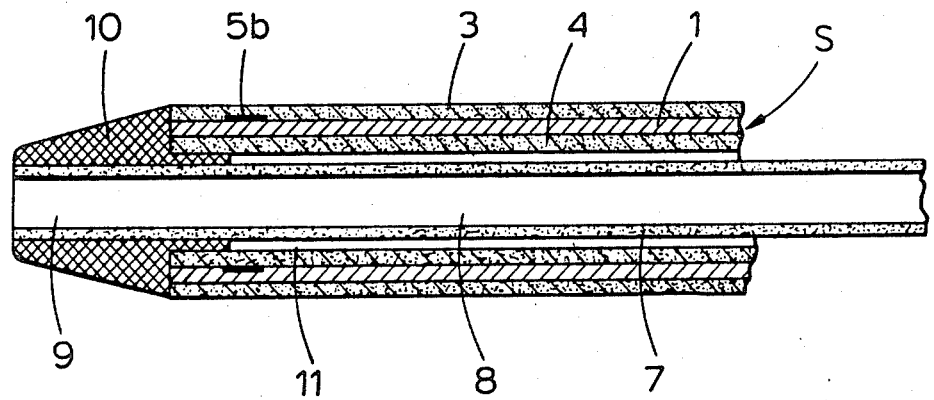
FIGS. 2 and 3 are schematic sectional views of the distal end portion of a modified form of the catheter of FIG. 1, also respectively illustrating the catheter in the deflated and inflated condition.
Figure 3:
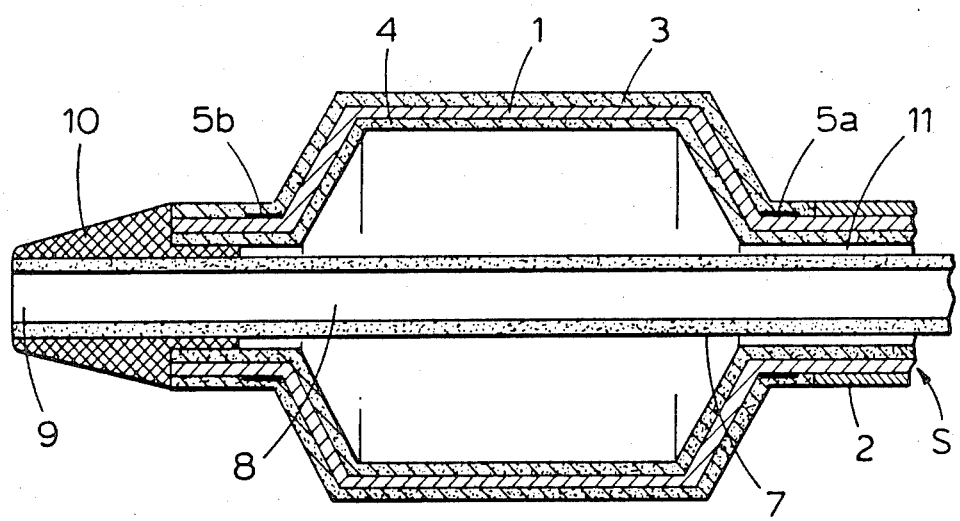
Figure 4:
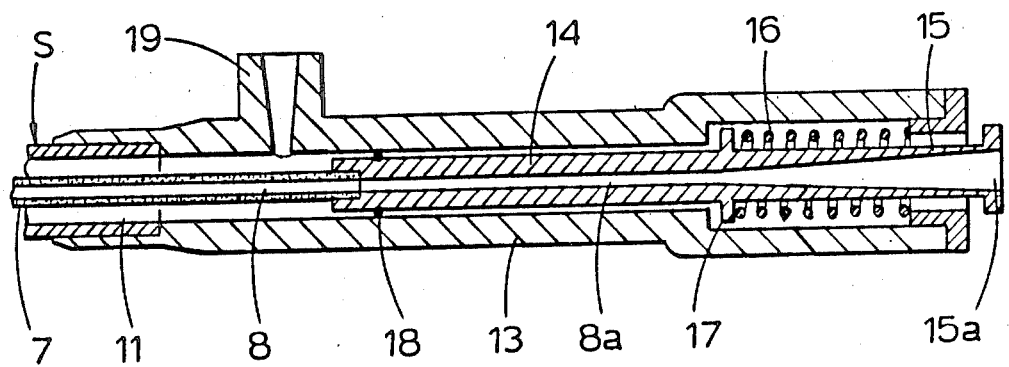
FIG. 4 is a schematic cross-section view through a mount attached to the proximal end of the catheter.

As shown in FIGS. 2,3 and 4, an inner tube 7, is arranged inside the shaft S. The inner tube 7 is of a semi-rigid material such as PVC. It is coaxial with the shaft S and is axially displaceable with respect to it. This tube 7 defines a central lumen 8 having an opening 9 at its distal end. If desired a lining (not shown) corresponding to the lining 6 of the FIG. 1 embodiment may be bonded to the coating 4 to reduce friction. The inner tube 7 is secured to the outer shaft S by means of a tip or plug 10 at the distal end of the catheter although, as previously stated, the tube 7 is axially displaceable with respect to the outer shaft S. As shown in FIGS. 2 and 3, the tip 10 tapers towards the distal end of the catheter. In addition to defining the central lumen 8, the inner tube 7 also defines an outer annular lumen 11 which serves as an inflation lumen through which fluid can pass to inflate the balloon portion of the catheter. The tip 10 also serves as a seal for the inflation lumen 11. The radio-opaque marker 5b is positioned at the distal extremity of the balloon.

A mount is provided at the proximal end of the catheter as shown in FIG. 4. This mount comprises a rigid or semi-rigid body 13 of metal or of plastics material secured to the outer coating of the shaft S. An inner piston member 14 is located inside the body and is bonded to the outside of the inner tube 7. The piston member 14 has a central passage 8a communicating with the central lumen 8 of the inner tube 7 so that liquid may be introduced to the lumen 8 via an opening 15a of a luer mount 15 or the like at the proximal end of the passage 8a. The liquid can flow through the lumen 8 and exit through the opening 9 at the distal end and then enter the patient. The passage 8a and lumen 8 also allows pressure monitoring to be carried out during the procedure and provides a means of inserting the catheter over a guide wire. A coil spring 16 surrounds the piston member inside the body and bears on a shoulder 17 of the piston member to urge it towards the distal end of the catheter. Means may also be provided to prevent the piston member 14 rotating with respect to the body 13. A flexible seal 18 seals the annular passage between the body 13 and the piston 14 and, therefore, the proximal end of the annular lumen 11.

A luer mount 19 or other suitable connection extends laterally from the body 13 and communicates with the interior of the body so that fluid can be passed into the outer annular lumen 11 of the catheter to enable the balloon portion to be inflated.

In use, the catheter may be inserted over a previously inserted guide wire into a blood vessel of a patient to be treated. The guide wire may then be removed. The balloon portion of the catheter is inflated by fluid pressure, conveniently produced by a suitable syringe. When the procedure has been completed, the fluid pressure is removed so that the balloon portion can resume its initial shape. When the fluid pressure has been removed, the piston member 14 will move towards the distal tip 10 assisted by the coil spring 16 to displace the inner tube 7 in the same direction to assist in returning the inflatable balloon portion to its non-inflated configuration as quickly as possible. Such movement also overcomes any residual tension set in the balloon portion of the catheter.

The catheter may conveniently be produced by a method in which the tube 1 is made by braiding around a suitable former. The former is previously provided with the inner coating 4 and, if required, the lining. The X-ray opaque members 5a and 5b are then positioned. The outer coating 3 is provided and may penetrate the braid and form a bond with the inner coating 4. The outer coating 2 is then applied to the major portion of the tube 1. The inner tube 7 and outer shaft S are secured to the piston member 14 and body 13 respectively. The distal tip 10 is then fitted.

The catheter of this invention may be modified for uses other than angioplasty procedures, but where dilatation is still required. In a modified catheter intended for general dilatation purposes, the catheter does not have an inner tube and the distal tip of the catheter is completely sealed. The proximal mount illustrated in FIG. 4 is not required in this modification but a luer mount with an integral stop-cock may be provided at the proximal end of the catheter to permit inflation fluid to be supplied to the catheter.

Figure 5:
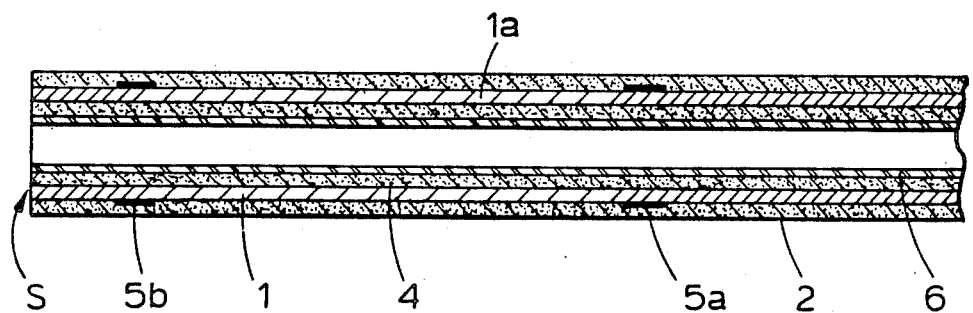
FIG. 5 is a schematic sectional view of a distal end portion of a further embodiment of a dilatation catheter according to the invention, showing a balloon portion in a deflated condition.

In the embodiment of the invention illustrated in FIG. 5 the braided tube 1 has a portion 1a in which there are fewer picks per unit length than the number of picks per unit length present in the rest of the tube 1. This makes this portion of the catheter readily inflatable. The number of picks per unit length in the rest of the tube, ie. outside the portion 1a is sufficient to prevent inflation. The coating 2 does not vary as between where it covers the portion 1a and where it covers the rest of the tube 1. The radio-opaque marker portion 5a is incorporated in the shaft at or near the junction where the portion 1a joins the rest of the tube 1. In respects other than those just referred to above the embodiment of FIG. 5 corresponds to that of FIG. 1.

Figure 7:
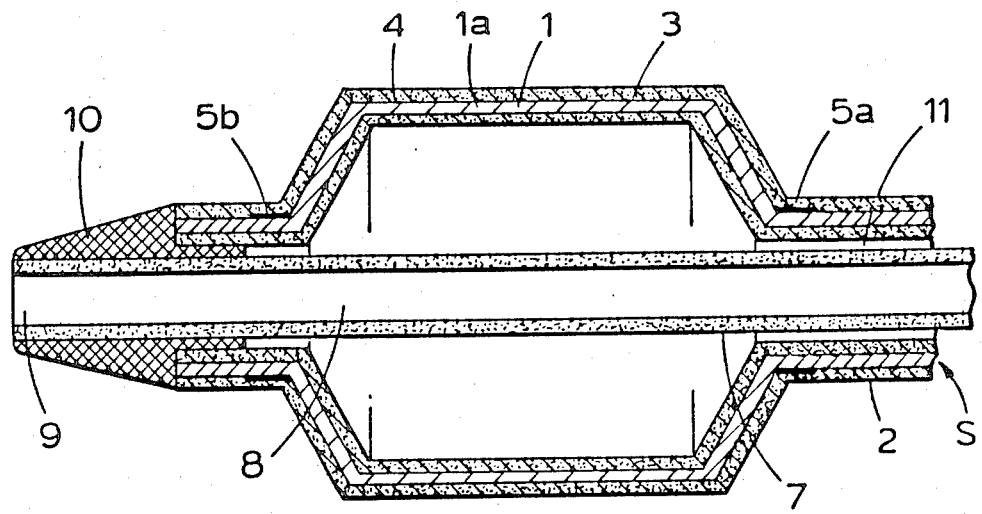
FIGS. 6 and 7 are schematic sectional views of the distal end portion of a modified form of the catheter of FIG. 5, also respectively illustrating the catheter in the deflated and inflated condition.
Figure 6:
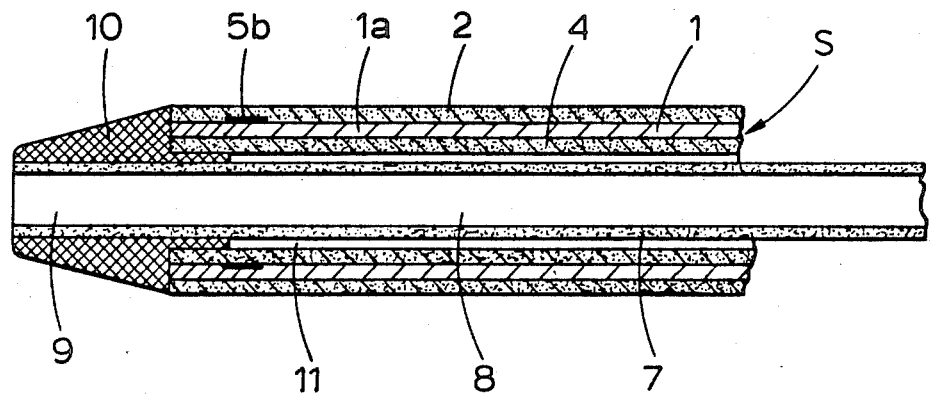

In the embodiment illustrated in FIGS. 6 and 7 the braided tube 1 also has a portion 1a in which there are fewer picks per unit length than the number of picks per unit length present in the rest of the tube 1. This makes this portion of the catheter readily inflatable, as can be seen from FIG. 7. The number of picks per unit length in the rest of the tube, ie. outside the portion 1a, is sufficient to prevent inflation. The coating 2 does not vary as between where it covers the portion 1a and where it covers the rest of the tube 1. The radio-opaque marker portion 5a is incorporated in the shaft at or near the junction where the portion 1a joins the rest of the tube 1. In respects other than those just referred to above the embodiment of FIGS. 6 and 7 corresponds to that of FIGS. 2 and 3. The embodiment of FIGS. 6 and 7 may be provided with the mount shown in FIG. 4.

We claim:

1. A dilatation catheter wherein a shaft of the catheter comprises a tube of material having an inelastic coating of semi-rigid material extending from the proximal end of the catheter over a major portion of the length of the shaft and also having an elastic outer coating extending over a minor portion of the length of the shaft, a passage in said tube communicating with said minor portion to provide a path for the application of inflating fluid thereto, whereby the said minor portion is inflatable in response to the application of the inflating fluid, said tube comprising braided material having a preselected maximum radial extension to limit the extent of inflation of said elastic coating, said major and minor portions being contiguous with each other and the coatings being bonded to said braided material.

2. A catheter as claimed in claim 1 wherein the cross-sectional area of both the major portion and the inflatable minor portion are the same whereby the profile of the catheter shaft is uniform over its entire length except for a tip at the distal end.

3. A catheter as claimed in claim 2 wherein the tip taper towards the distal end.

4. A catheter as claimed in claim 1 wherein an inner tube of smaller diameter than said shaft which is open at both ends of the catheter extends through the shaft thereby to define a central lumen and an outer annular lumen, between said inner tube and said shaft, sealing means sealing one end of said minor portion to said inner tube, means communicating with the annular lumen being provided to enable a fluid for inflating the said minor portion to be supplied to the outer annular lumen.

5. A catheter as claimed in claim 4 wherein the inner tube is displaceable axially with respect to the shaft.

6. A catheter according to claim 4, wherein a tip is secured to the outer shaft internally of the distal end thereof, the inner tube being also engaged in the tip.

7. A catheter according to claim 4 wherein a mount is fitted at the proximal end of the shaft, said mount comprising a body secured to the shaft; a piston member is arranged inside the body and is secured to the inner tube of the shaft, said piston member having a passage through which liquid can pass to or from the inner tube; spring means for urging the piston member towards the distal end of the shaft; a flexible seal between the piston and the body and a connection leading through the body to the annular lumen to permit said inflation fluid to be supplied to the annular lumen whereby the catheter can be inflated over the said minor portion.

8. A catheter according to claim 7 wherein the piston member is fixed against rotation with respect to the body.

9. A catheter as claimed in claim 1 wherein the tube of braided material is provided with an inner tube of elastic material extending the entire length of the catheter.

10. A catheter as claimed in claim 1 wherein the braided material has fewer picks per inch over the portion of its entire length within the minor portion having the elastic outer coating.

11. A catheter according to claim 1, wherein a radio-opaque marker is arranged between the tube of braided material and the outer coating.

12. A catheter according to claim 11, wherein radio-opaque markers are provided at each end of the inflatable portion.

13. A catheter according to claim 1 wherein the catheter has distal and proximal ends and said minor portion is located at or near the distal end.

14. A dilatation catheter wherein a shaft of the catheter comprises a tube of material having an inelastic coating of semi-rigid material extending from the proximal end of the catheter over a major portion of the length of the shaft and also having an elastic outer coating extending over a minor portion of the length of the shaft, a passage in said tube communicating with said minor portion to provide a path for the application of inflating fluid thereto, whereby the said minor portion is inflatable in response to the application of the inflating fluid, said tube comprising braided material having a preselected maximum radial extension to limit the extent of inflation of said elastic coating, said catheter further comprising an inner tube of impervious elastic material located inwardly of the braided material and extending over the length of the catheter.

15. A catheter as claimed in claim 14 wherein the cross-sectional area of both the major portion and the inflatable minor portion are the same whereby the profile of the catheter shaft is uniform over its entire length except for a tip at the distal end.

16. A catheter as claimed in claim 15 wherein the tip tapers towards the distal end.

17. A catheter as claimed in claim 14, wherein a further inner tube of smaller diameter than said shaft which is open at both ends of the catheter extends through the shaft thereby to define a central lumen and an outer annular lumen, between said further inner tube and said shaft, sealing means sealing one end of said minor portion to said further inner tube, means communicating with the annular lumen being provided to enable a fluid for inflating the said minor portion to be supplied to the outer annular lumen.

18. A catheter as claimed in claim 17 wherein said further inner tube is displaceable axially with respect to the shaft.

19. A catheter according to claim 17, wherein a tip is secured to the outer shaft internally of the distal end thereof, the further inner tube being also engaged in the tip.

20. A catheter according to claim 17 wherein a mount is fitted at the proximal end of the shaft, said mount comprising a body secured to the shaft; a piston member is arranged inside the body and is secured to the further inner tube of the shaft, said piston member having a passage through which liquid can pass to or from the further inner tube; spring means for urging the piston member towards the distal end of the shaft; a flexible seal between the piston and the body and a connection leading through the body to the annular lumen to permit said inflation fluid to be supplied to the annular lumen whereby the catheter can be inflated over the said minor portion.

21. A catheter according to claim 20 wherein the piston member is fixed against rotation with respect to the body.

22. A catheter as claimed in claim 14 wherein the braided material has fewer picks per inch over the portion of its length within the minor portion having the elastic outer coating.

23. A catheter according to claim 14, wherein a radio-opaque marker is arranged between the tube of braided material and the outer coating.

24. A catheter according to claim 23, wherein radio-opaque markers are provided at each end of the inflatable portion.

25. A catheter according to claim 14 wherein the catheter has distal and proximal ends and said minor portion is located at or near the distal end.

26. A dilatation catheter wherein a shaft of the catheter comprises a tube of braided material having a coating bonded to the outer surface thereof, having a coating bonded to the outer surface thereof, at least a portion of which is elastic the catheter having a major portion of its length over which the braided material has more picks per unit length than it has over a minor portion said elastic portion extending over said minor portion, a passage in said tube communicating with said minor portion to provide a path for the application of inflating fluid thereto, whereby the said minor portion is inflatable in response to the application of the inflating fluid, and said major portion is not, said major and minor portions being contiguous with one another.

27. A catheter as claimed in claim 26 wherein the cross-sectional area of both the major portion and the inflatable minor portion are the same whereby the profile of the catheter shaft is uniform over its entire length except for a tip at a distal end of the catheter.

28. A catheter as claimed in claim 27 wherein the tip tapers towards the distal end.

29. A catheter as claimed in claim 26, wherein an inner tube of smaller diameter than said shaft which is open at both ends of the catheter extends through the shaft thereby to define a central lumen and an outer annular lumen, between said inner tube and said shaft, sealing means sealing one end of said minor portion to said inner tube, means communicating with the annular lumen being provided to enable a fluid for inflating the said minor portion to be supplied to the outer annular lumen.

30. A catheter as claimed in claim 29 wherein the inner tube is displaceable axially with respect to the shaft.

31. A catheter according to claim 29, wherein a tip is secured to the outer shaft internally of the distal end thereof, the inner tube being also engaged in the tip.

32. A catheter according to claim 29 wherein a mount is fitted at the proximal end of the shaft, said mount comprising a body secured to the shaft; a piston member is arranged inside the body and is secured to the inner tube of the shaft, said piston member having a passage through which liquid can pass to or from the inner tube; spring means for urging the piston member towards the distal end of the shaft; a flexible seal between the piston and the body and a connection leading through the body to the annular lumen to permit inflation fluid to be supplied to the annular lumen whereby the catheter can be inflated over the said minor portion.

33. A catheter according to claim 32 wherein the piston member is fixed against rotation with respect to the body.

34. A catheter as claimed in claim 26 wherein the tube of braided material is provided with an inner tube of impervious elastic material extending the entire length of the catheter.

35. A catheter according to claim 26, wherein a radio-opaque marker is arranged between the tube of braided material and the outer coating.

36. A catheter according to claim 35, wherein radio-opaque markers are provided at each end of the inflatable portion.

37. A catheter according to claim 26, wherein the catheter has distal and proximal ends and said minor portion is located at or near the distal end.

38. A dilatation catheter wherein a shaft of the catheter comprises a tube of braided material having a coating on the outer surface thereof, at least a portion of which is elastic the catheter having a major portion of its length over which the braided material has more picks per unit length than it has over a minor portion, said elastic portion extending over said minor portion, a passage in said tube communicating with said minor portion to provide a path for the application of inflating fluid thereto, whereby the said minor portion is inflatable in response to the application of the inflating fluid, and said major portion is not, said catheter further comprising an inner tube of impervious elastic material located inwardly of the braided material and extending over the length of the catheter.

39. A catheter as claimed in claim 38 wherein the cross-sectional area of both the major portion and the inflatable minor portion are the same whereby the profile of the catheter shaft is uniform over its entire length except for a tip at the distal end.

40. A catheter as claimed in claim 39 wherein the tip tapers towards the distal end.

41. A catheter as claimed in claim 38, wherein a further inner tube of smaller diameter than said shaft which is open at both ends of the catheter extends through the shaft thereby to define a central lumen and an outer annular lumen, between said further inner tube and said shaft, sealing means sealing one end of said minor portion to said further inner tube, means communicating with the annular lumen being provided to enable a fluid for inflating the said minor portion to be supplied to the outer annular lumen.

42. A catheter according to claim 41, wherein a tip is secured to the outer shaft internally of the distal end thereof, the further inner tube being also engaged in the tip.

43. A catheter according to claim 41 wherein a mount is fitted at the proximal end of the shaft, said mount comprising a body and is secured to the shaft; a piston member is arranged inside the body and is secured to the further inner tube of the shaft, said piston member having a passage through which liquid can pass to or from the further inner tube; spring means for urging the piston member towards the distal end of the shaft; a flexible seal between the piston and the body and a connection leading through the body to the annular lumen to permit said inflation fluid to be supplied to the annular lumen whereby the catheter can be inflated over the said minor portion.

44. A catheter according to claim 43, wherein the piston member is fixed against rotation with respect to the body.

45. A catheter as claimed in claim 41, wherein said further inner tube is displaceable axially with respect to the shaft.

46. A catheter according to claim 38, wherein a radio-opaque marker is arranged between the tube of braided material and the outer coating.

47. A catheter according to claim 46, wherein radio-opaque markers are provided at each end of the inflatable portion.

48. A catheter according to claim 38, wherein the catheter has distal and proximal ends and said minor portion is located at or near the distal end.

* * * * *